(12) United States Patent
Thoes et al.

(10) Patent No.: US 9,671,387 B2
(45) Date of Patent: Jun. 6, 2017

(54) TEST SYSTEM

(75) Inventors: Bruno Thoes, Quierschied (DE); Karl Miltner, Frankenthal (DE); Peter Hess, Worms (DE); Guenter Ihle, Mauer (DE); Martin Koch, Viernheim (DE); Joerg Scherer, Aalen (DE); Klaus-Dieter Sacherer, Kirchheim (DE); Ralf Piegsa, Stuttgart (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1267 days.

(21) Appl. No.: 12/910,425

(22) Filed: Oct. 22, 2010

(65) Prior Publication Data
US 2011/0263957 A1 Oct. 27, 2011

Related U.S. Application Data

(63) Continuation of application No. PCT/EP2009/054702, filed on Apr. 21, 2009.

(30) Foreign Application Priority Data

Apr. 23, 2008 (EP) ..................... 08155024

(51) Int. Cl.
*A61B 5/145* (2006.01)
*G01N 21/01* (2006.01)
(Continued)

(52) U.S. Cl.
CPC ... *G01N 33/48764* (2013.01); *A61B 5/14532* (2013.01); *A61B 5/1455* (2013.01);
(Continued)

(58) Field of Classification Search
CPC ........ A61B 2562/0295; A61B 5/14532; A61B 5/1455; G01N 33/48764;
(Continued)

(56) References Cited

U.S. PATENT DOCUMENTS 6,997,343 B2 2/2006 May et al.
2008/0008989 A1* 1/2008 Sacherer .................. 435/4
2008/0049227 A1* 2/2008 Sacherer .................. 356/445

FOREIGN PATENT DOCUMENTS

EP 0353592 B1 4/1996
EP 1424040 A1 6/2004
(Continued)

OTHER PUBLICATIONS

International Preliminary Report on Patentability from corresponding PCT/EP2009/054702 (German).

*Primary Examiner* — Jennifer Wecker

(57) ABSTRACT

The invention concerns a test system for carrying out blood sugar tests with a diagnostic tape cassette which comprises a windable analytical test tape for detecting an analyte and a cassette housing accommodating the test tape, and a test device which has a device housing for inserting and removing the tape cassette and a measuring unit for detecting the analyte on the test tape. According to the invention it is proposed that the tape cassette can be detachably fastened by positioning elements on a platform mounted in the device housing and that the measuring unit is rigidly attached on the platform or can be engaged therewith.

18 Claims, 2 Drawing Sheets

(51) Int. Cl.
    *G01N 33/50*         (2006.01)
    *G01N 33/487*       (2006.01)
    *G01N 33/00*         (2006.01)
    *C12Q 1/00*          (2006.01)
    *G01N 21/47*         (2006.01)
    *B01L 3/00*           (2006.01)
    *G01N 35/00*         (2006.01)
    *G01N 21/64*         (2006.01)
    *A61B 5/1455*      (2006.01)

(52) U.S. Cl.
    CPC . *A61B 2562/0295* (2013.01); *B01L 3/502715* (2013.01); *B01L 2300/0812* (2013.01); *B01L 2300/0825* (2013.01); *G01N 35/00009* (2013.01); *G01N 2021/478* (2013.01); *G01N 2021/6436* (2013.01)

(58) Field of Classification Search
    CPC ..... G01N 2021/6436; G01N 35/00009; G01N 2021/478; B01L 2300/0825; B01L 2300/0812; B01L 3/502715
    USPC .... 422/68.1, 82.05, 401, 430; 600/573, 347, 600/365
    See application file for complete search history.

(56) References Cited

FOREIGN PATENT DOCUMENTS

| EP | 1878379 A1 | 1/2008 |
|---|---|---|
| WO | 2008/022999 A1 | 2/2008 |

\* cited by examiner

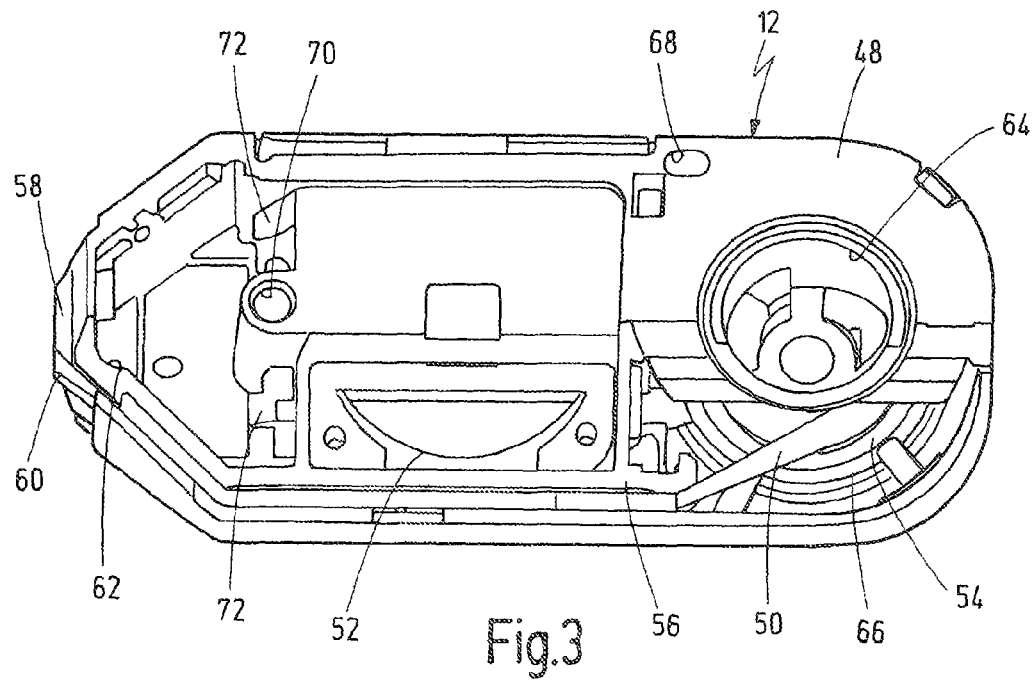
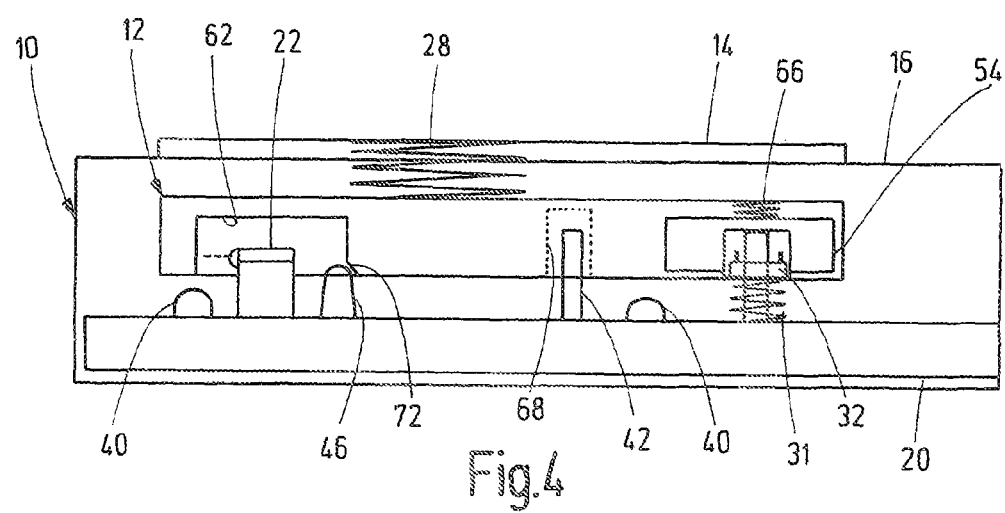

TEST SYSTEM

CLAIM OF PRIORITY

The present application is a continuation application based on and claiming priority to international application PCT/EP2009/054702, filed Apr. 21, 2009, which claims the priority benefit of European Application No. 08155024.6, filed Apr. 23, 2008, each of which are hereby incorporated by reference in their respective entireties.

TECHNICAL FIELD OF THE INVENTION

The invention concerns a test system in particular for carrying out blood sugar tests with a diagnostic tape cassette which comprises a windable analytical test tape for detecting an analyte and a cassette housing accommodating the test tape, and a test device which has a device housing for inserting and removing the tape cassette and a measuring unit for detecting the analyte on the test tape, such as an optical measuring unit.

BACKGROUND

Individual test strips have previously been used in practice for the self-diagnosis of diabetics and are examined electrochemically or photometrically after the application of a small amount of sample in order to determine the glucose content in a blood sample as exactly and reliably as possible. In this process the measuring strips are usually held during the measurement by holding structures which are parts of the housing of a hand-held device. This should ensure that the measuring field on the test strip is situated relatively accurately in relation to, for example in an optical system, the scanning optical measurement system because this is also attached to the housing components. The used individual strips are removed from the device after completion of the measurement and are disposed of By doing without disposal within the device, space is saved in a small hand-held device and the housing which has relatively large construction tolerances does not have to be involved in further primary system functions. In this connection it should be taken into consideration that the device housing usually has to fulfill several functions simultaneously: covering (protection of the system), design representation, positioning of the individual components relative to one another and mechanical stiffening. This shift of many functions into one component generates several contradictory requirements and has the effect that the implementation of the primary functionality (covering and design representation) is made more difficult while at the same time the other functional demands—mechanical stiffening and precise relative positioning of the system assembly units—are insufficiently achieved.

In order to achieve additional application advantages, it has already been proposed that a plurality of tests be provided and disposed of again on a test tape in the form of a tape cassette. Such tape cassettes are intended to be inserted as a disposable part into compact hand-held devices in order to allow all necessary analytical steps to be carried out automatically and rapidly.

On this basis the object of the invention is to further improve the test systems proposed in the prior art and achieve in a compact design a high positioning accuracy and particular user friendliness when using tape cassettes.

SUMMARY

This object and others that will be appreciated by a person of ordinary skill in the art have been achieved according to the embodiments of the present invention disclosed herein. In one embodiment, the present invention comprises a test system for carrying out blood sugar tests with a diagnostic tape cassette which comprises a windable analytical test tape for detecting an analyte and a cassette housing accommodating the test tape, and a test device which has a device housing for inserting and removing the tape cassette and a measuring unit for detecting the analyte on the test tape, wherein the tape cassette can be detachably fastened by means of positioning elements on a platform mounted in the device housing and that the measuring unit is fixedly attached on the platform or can be engaged therewith.

In a further embodiment, the present invention relates to a test system for carrying out blood sugar tests with a diagnostic tape cassette which comprises a windable analytical test tape for detecting an analyte and a cassette housing accommodating the test tape, and a test device which has a device housing for inserting and removing the tape cassette and a measuring unit for detecting the analyte on the test tape, wherein when the tape cassette is inserted, it moves from a loose insertion position into a defined fixed measuring position in the device under the action of a spring arrangement.

The embodiments of the present invention are based on the idea of carrying out the measuring process geometrically directly between the measuring unit and a disposable connected thereto by a coupling component. Accordingly it is proposed according to the invention that the tape cassette can be detachably fastened by means of positioning elements on a platform mounted in the device housing and that the measuring unit is fixedly attached on the platform or can be engaged therewith. In this manner the measuring unit is arranged in a defined relative position in relation to the fastened tape cassette without directly involving housing components. The platform creates a sort of mechanical backbone which allows the attachment or docking of the measuring unit and enables a tape magazine to be positioned reproducibly within narrow limits.

The platform advantageously forms the base of a cassette compartment in the device housing so that the user can easily insert and remove the tape cassette.

Another embodiment provides that the platform is formed by a mechanically self-stable support plate which is held in the device housing by connecting means. This can be manufactured particularly advantageously when the platform comprises an outsell molding part having a metal support and plastic parts formed thereon.

In order to create a tilt-free flat support for the tape cassette, the positioning elements typically comprise several point-shaped or linear raised supports that are disposed on the platform. In one embodiment, the positioning elements comprise three such raised supports. Further degrees of freedom of movement can be limited by means of the fact that positioning elements arranged on the platform can be engaged in pairs with positioning elements of the tape cassette while eliminating displacement play. Such a displacement play which should enable a simple prepositioning is advantageously between 1 mm and 3 mm.

In one embodiment the positioning elements comprise at least one positioning pin the base of which is cylindrical and tapers towards its free end in order to thus enable an intuitive placement of the cassette by the user. In this connection the positioning elements typically have at least one oblong hole or round hole for the engagement of a positioning pin.

A further aspect of the present invention is that when the tape cassette is inserted, it passes from a loose insertion position into a defined fixed measuring position in the device under the action of a spring arrangement. This enables a particularly simple handling by the user in which case such locking of the cassette that is switched in a path-dependent manner can also be simply implemented in the small installation space of a hand-held device.

Another improvement in handling results from the fact that the tape cassette can be inserted into the test device in a movement in an uni-axial motion in the direction of an insertion axis.

In order to substantially automate the end positioning, in one embodiment the spring arrangement has at least one compression spring that can be compressed in the direction of the insertion axis and the spring arrangement can be actuated by closing a housing cover of the test device. This can be achieved by a compression spring of the spring arrangement that projects from the inner side of a housing cover of the test device and is supported on the inserted tape cassette when the housing cover is closed.

In order to achieve further functions, in other embodiments a compression spring of the spring arrangement engages with a take-up spool of the tape cassette.

The desired end position can be defined within narrow tolerance limits by means of the fact that the spring arrangement has at least one pressure spring which can be deflected crosswise to the insertion axis in order to make a clamp connection of the tape cassette. Another improvement provides that the pressure spring, such as a leaf spring, can be pretensioned by a sloping face of the tape cassette.

In order to avoid wedging in the device, in yet other embodiments the inserted tape cassette is spring-loaded at least two spaced apart support points.

A particularly compact construction can be achieved by means of the fact that in the direction of the insertion axis the measuring unit engages in a free space of the tape cassette inserted into the test device. In this connection, for an exemplary optical measurement system the measuring unit can be formed by a reflection-photometric measuring head mounted on the platform where the optical path of the measuring head runs crosswise to the direction of tape transport of the tape cassette located in the measuring position.

The tape cassette can advantageously be connected to a tape drive of the device by means of a coupling where the coupling has form-fit elements which upon insertion of the tape cassette can be moved by means of a deflection movement from a separate initial position into a rotationally locked engagement position. Dead positions of the form-fit elements can be avoided or overcome by the deflection movement. In this manner a blocking of the cassette during insertion can be prevented. At the same time it ensures that a tape cassette held under permanent tape tension for a defined test positioning can easily be inserted into the device.

The invention also concerns a tape cassette with a supply spool and a take-up spool as well as a tape guide for the defined transport of an analytical test tape between the spools wherein the tape cassette is designed or is suitable and intended to be used as a disposable in a test system according to the present invention.

BRIEF DESCRIPTION OF THE DRAWINGS

The following detailed description of the embodiments of the present invention can be best understood when read in conjunction with the following drawings, where like structure is indicated with like reference numerals and in which:

FIG. 3 shows a tape cassette as a test means for the blood sugar test device in a partially broken view from below.

FIG. 4 shows the test system consisting of blood sugar test device and inserted tape cassette in a diagrammatic view.

Figure 1:
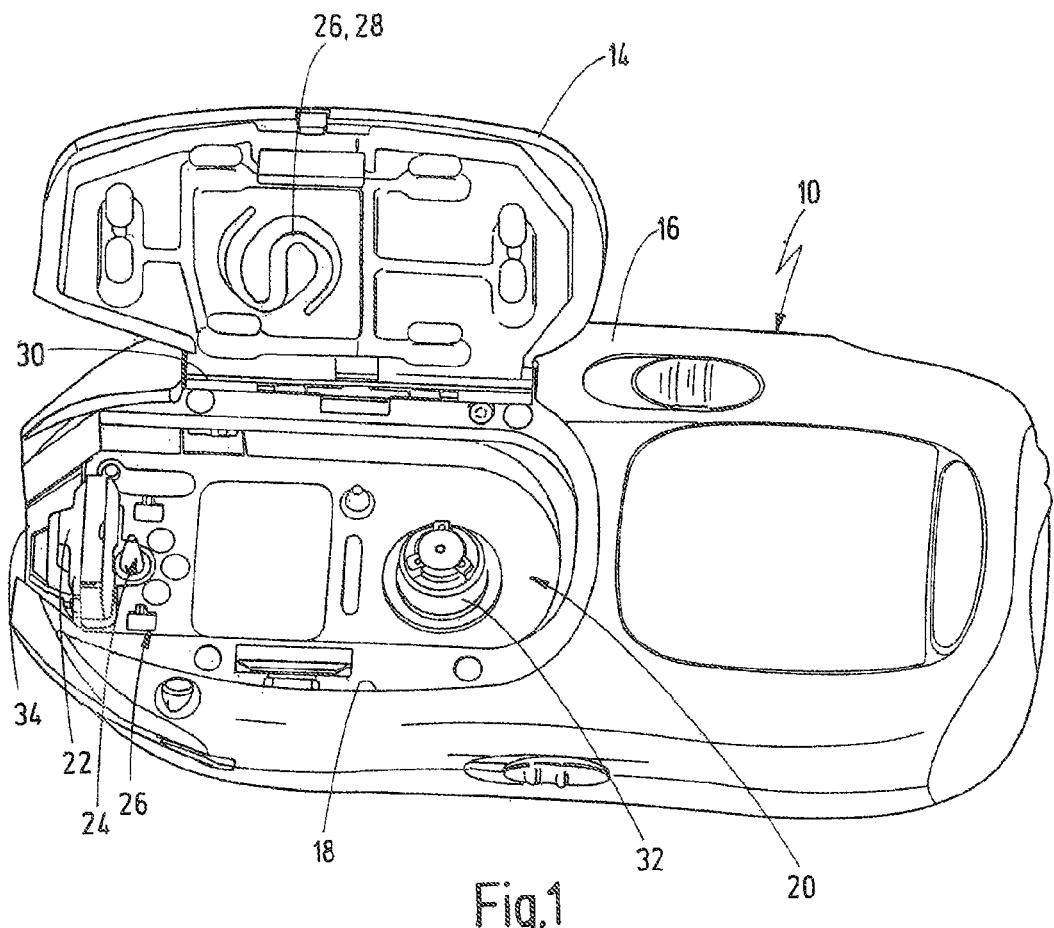
FIG. 1 shows a blood sugar test device with an integrated platform for receiving a tape cassette in a perspective diagram.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses. Embodiments of the present invention may be set forth in the context of an optical measurement system, but should be understood to be applicable to other measurement systems, such as electrochemical, with appropriate system-specific modifications as will be understood and appreciated by those of ordinary skill in the art in view of the disclosure herein.

The blood sugar test device 10 shown in the drawing enables, in the form of a hand-held device, a tape cassette 12 to be inserted as an analytical consumable in order to carry out a plurality of self-tests using blood samples collected locally by the patients themselves.

FIG. 1 shows the blood sugar test device 10 with an opened cover 14 of the housing 16 to release the cassette compartment 18. The bottom of the cassette compartment 18 is delimited by a platform 20 which forms a device chassis for the defined mounting of an optical measuring unit 22 and for accurate positioning of the tape cassette 12 relative to the measuring unit. For this purpose several positioning elements 24 are arranged on the platform 20 and on the tape cassette 12 which in conjunction with a spring arrangement 26 ensure not only proper positioning but also a simple handling when the cassette is exchanged.

The spring arrangement 26 comprises a cover spring 28 which, in the form of a ring structure projecting from the inner side, is punched out of sheet material and pre-bent. The cover 14 hinged on a hinge 30 can be swung towards an inserted tape cassette 12 such that the cover spring 28 exerts a spring force onto the tape cassette which is directed towards the platform 20. On the platform 20 a rotary drive pin 32 of a tape drive that is axially spring-loaded by coil springs 31 can be engaged with the tape cassette. Test tape material can be transported by the tape drive into the area of a housing opening 34 in order to carry out a glucose test there after blood fluid has been applied. Details of the test procedure are for example known from EP-A 1878379 the disclosure of which is hereby incorporated by reference herein in its entirety.

Figure 2:
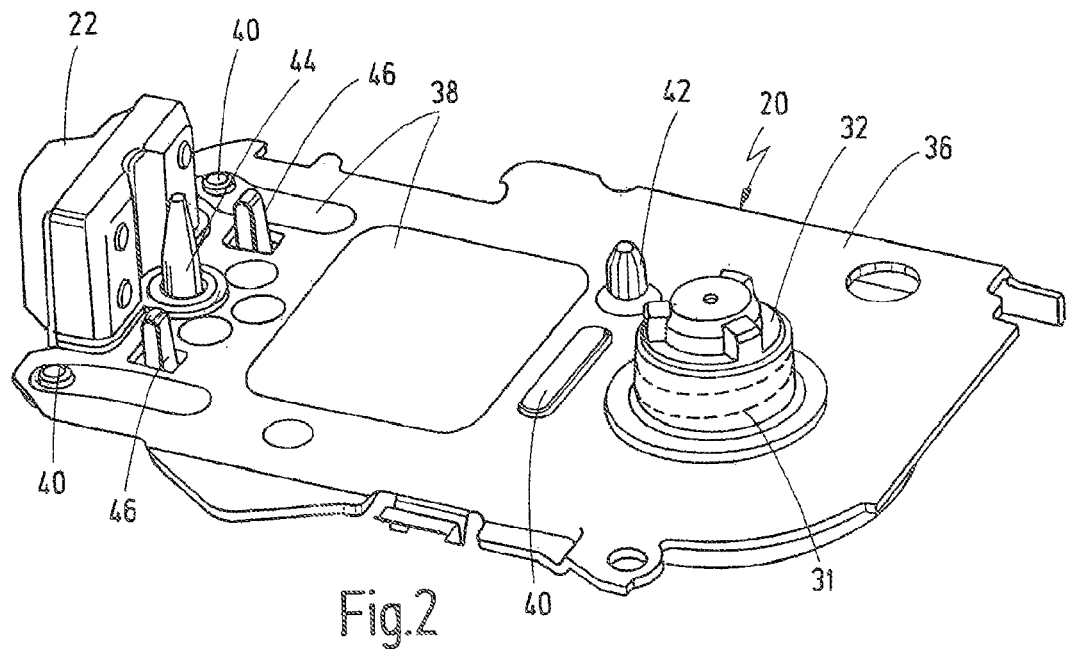
FIG. 2 shows the platform according to FIG. 1 in an enlarged perspective view.

FIG. 2 shows the platform 20 with the functional parts assembled thereon as an independent structural unit of the test device 10. The outsert technique is used to form the platform 20 as an outsert molding part from a metal support 36 and plastic parts 38 injection-molded thereon. In the outsert technique the metal support is placed in the mold cavity of a closable molding tool and joined with hardenable plastic compound, by a process such as injection molding. In this process the formed plastic is permanently anchored to the metal support by undercuts and openings. The process as such is known to a person skilled in the art so that further details of the process do not have to be described here.

As a central element in the test system, the platform 20 can incorporate all functional parts to ensure the essential device functions and thus become a central assembly. Then all functions can be expediently independently tested on this central assembly during the course of device manufacture. All components necessary for the measuring function of the measuring unit 22 can be assembled on the platform 20 so that the measuring function can be checked independently of a mounting in the device housing 16. Furthermore, changes in the design of, for example, the device housing 16 do not necessarily have to be accompanied by a geometric change in the platform 20 and the functional parts assembled thereon.

A plurality of upward-projecting plastic supports 40 are molded onto the platform 20 to support the tape cassette 12 in a tilt-free manner. In the illustrated embodiment, three such supports 40 are provided, which span a positioning plane in a geometrically unequivocal manner. It is locked in this plane by means of two pins 42, 44 which engage in openings of the tape cassette 12. In this embodiment as elucidated in more detail below, two pressure springs 46 in the form of U-shaped leaf springs of the spring arrangement 26 ensure a clamping connection in the intended end position.

FIG. 3 shows the tape cassette 12 from below as a disassembled longitudinal half. A test tape 50 can be pulled from a storage spool 52 and wound onto a take-up spool 54 in the cassette housing 48. The test tape 50 is deflected by a tape guiding frame 56 over an application tip 58 between the spools in order to allow body fluid (blood or tissue fluid) to be applied to the front and a reflectometric measurement to be carried out on the rear side. For this purpose test fields 60 provided with dry chemicals which react with the analyte (glucose) in the applied blood fluid are mounted in sections on the test tape 12 and, when the rear side is illuminated they result in a measurable change in the light that is radiated back. A free space 62 is kept free behind the application tip 58 to enable the measuring head 22 to engage for the rear side measurement.

In order to advance the test tape 50, the hub 64 of the take-up spool 54 is connected with the drive pin 32 in a rotationally locked manner. A pressure spring 66 supported on the cover side on the cassette housing 48 acts in this connection against the drive pin spring 31.

An oblong hole 68 and a round hole 70 for plugging onto the pins 42, 44 of the platform 20 are provided as further positioning elements in the cassette housing 48. When the tape cassette is placed thereon the pins with their tapered tip firstly ensure a large degree of play whereas in the area of the cylindrical base of the pin only a reduced air gap still remains free. Two sloping faces 72 for the pressure springs 46 are formed on the cassette housing to eliminate this remaining clearance.

As shown in FIG. 4 the arrangement described above enables a simplified insertion of the tape cassette 12 into the test device 10 and at the same time a high positioning accuracy in the intended measuring position with a path-dependent switching of the states "loose" and "fixed" of the cassette in the device. At first the tape cassette 12 can be inserted directly into the cassette compartment 18 by the user in a linear movement that is perpendicular to the platform 20 and still be loosely placed on the tapered pins 42, 44. Subsequently by closing the housing cover 14, the cassette is pressed into its desired end position and locked there under the force of the cover spring 28. In this process the various positioning elements and springs act in a mutually coordinated manner in order to position the cassette within narrow tolerances relative to the measuring unit 22.

The supports 40, 42 define the positioning plane and thus reduce three of the six possible degrees of freedom for movement potential of the tape cassette 12. The combination of pin 44 and round hole 70 reduces two further degrees of freedom. The remaining rotational degree of freedom is prevented by the pin 42 in conjunction with the oblong hole 68.

In order to avoid an initial jamming during insertion, the positioning element pairs 44, 70 and 42, 68 allow a displacement play of about 1 mm in the cassette longitudinal direction. This displacement play is determined by the difference in diameters between the round hole 70 and pin 44 while the oblong hole 68 has a somewhat larger hole length. In order to ensure a reproducible end position, the pressure springs 46 which run up against the bevels 72 ensure a clamping tangential engagement of the pin 44 at its base. In this connection the drive pin 32 has sufficient additional transverse play and the frontal drivers make a rotationally fixed form fit with the hub 64 under the force of the springs 31, 66.

In the inserted end position or measuring position, the optical path of the measuring head 22 runs at right angles to the direction of tape transport of the tape cassette and a reproducible detection of the test field is ensured by the very precise positioning.

As already mentioned, the take-up spool 54 forms a form-fitting coupling with the drive pin 32 when the cassette 12 is inserted. Generally it is advantageous when the driving side (input) and the driven side (output) of the coupling each have elements which, on the one hand, enable the two sides to be centered relative to one another (coaxial alignment) and, on the other hand, translate a rotational movement of the input side into a rotational movement of the output side. In this connection a rotationally locked connection can be ensured by form-fit elements which are able to generate a form-fit with their respective counterpart. In this process an element of the input side engages into a gap between two elements of the output side. When the cassette is inserted, the form-fit elements may not stand "tooth to gap" but rather "tooth to tooth". This orientation of the elements of the input and output side of the form-fit coupling would hold up or block the insertion process in such a manner that the cassette would not reach the desired end position in the device. Consequently the user could not put the device into operation without an additional remedy. In order to avoid this, one of the form-fit elements is designed to yield. In the illustrated embodiment the yielding element is a part of the device 10 in the form of a driver 32. The selected yielding movement is axial. The yielding element is axially spring loaded by means of the drive spring 31 configured, for example, as a cylindrical spring.

Other embodiments for this function are conceivable irrespective of the selected embodiment example. The yielding element could also be part of the cassette (e.g. as a part within the hub 64). The yielding movement could take place radially or be rotatively by "forced twisting" of the form-fit elements during the insertion process so that the form-fit elements twist from the position "tooth to tooth" into the position "tooth to gap". The yielding element can be a separate component (with an associated spring) as in the present case but it can also be a part of the input or also output side such that by design and/or choice of material a yielding during insertion as well as the transmission of torque during operation can take place.

In order to remove a used tape cassette 12, the user only has to open the housing cover 14 in order to thus trigger an automatic lifting of the cassette by the pre-tensioned springs 31, 66 and 46. The interaction of the springs ensures that the cassette is lifted in parallel at two spaced-apart support points thus avoiding wedging in the cylindrical area of the positioning pins 42, 44. Subsequently it is possible to allow the cassette 12 to fall out of the cassette compartment 18 when the cover 14 points downwards solely under the force of gravity without additional application of force.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A test system for carrying out blood sugar tests, comprising:
    a diagnostic tape cassette comprising a windable analytical test tape for detecting an analyte and a cassette housing accommodating the test tape, wherein the cassette housing comprises a plurality of tape cassette positioning elements; and
    a test device comprising:
        a device housing configured for inserting and removing the tape cassette,
        an associated measuring unit for detecting the analyte on the test tape, and
        a platform permanently integrated or mounted as a device element in a base of a cassette compartment in the device housing, the platform comprising a rotary drive pin of a tape drive and a plurality of platform positioning elements,
    wherein the tape cassette, when inserted into the cassette compartment of the device housing, is detachably fastened to the platform by means of the plurality of platform positioning elements and the rotary drive pin,
    wherein the plurality of platform positioning elements comprises one or more raised supports and one or more positioning pins, wherein the one or more raised supports are disposed on a surface of the platform and are configured to provide a tilt-free support for an inserted tape cassette, wherein the one or more positioning pins are disposed on the surface of the platform and are pairable with at least one of the plurality of tape cassette positioning elements and are configured to nullify displacement play, and wherein the displacement play is between 1 mm and 3 mm, and
    wherein the measuring unit is fixedly attached on the platform or can be engaged therewith.

2. The test system according to claim 1, wherein the platform is defined by a mechanically self-stable support plate that is held in the device housing by connecting means.

3. The test system according to claim 2, wherein the platform comprises an outsert molding part comprising a metal support and plastic parts formed thereon.

4. The test system according to claim 1, wherein the one or more positioning pins have a cylindrical base and taper towards a free end.

5. The test system according to claim 4, wherein the plurality of tape cassette positioning elements comprises at least one oblong hole or round hole for engaging or pairing with at least one positioning pin.

6. The test system according to claim 1, wherein the test device further comprises a housing cover comprising a spring arrangement projecting from an inner side of the housing cover and configured to convey the tape cassette from a loose insertion position into a defined fixed measuring position in the device during insertion of the tape cassette.

7. A test system for carrying out blood sugar tests with a diagnostic tape cassette, comprising:
    the diagnostic tape cassette comprising:
        a windable analytical test tape for detecting an analyte,
        a take-up spool configured for advancing the analytical test tape from a supply spool, and
        a cassette housing accommodating the test tape; and
    a test device comprising:
        a device housing configured for inserting and removing the diagnostic tape cassette, an associated measuring unit for detecting the analyte on the test tape, and
        a platform permanently integrated or mounted as a device element in a base of a cassette compartment in the device housing, the platform comprising a rotary drive pin of a tape drive, wherein at least part of the rotary drive pin is axially spring loaded by at least one coil spring and is configured to engage the take-up spool or the supply spool of the diagnostic tape cassette, and wherein the measuring unit is fixedly attached on the platform or can be engaged therewith, and
    wherein when the tape cassette is inserted, it moves from a loose insertion position into a defined fixed measuring position in the device under the action of a spring arrangement comprising at least one compression spring projecting from an inner side of the housing cover that is configured to be compressed in the direction of an insertion axis.

8. The test system according to claim 7, wherein the tape cassette can be inserted into the test device in a uni-axial motion in the direction of the insertion axis.

9. The test system according to claim 7, wherein the spring arrangement can be actuated by closing the housing cover of the test device.

10. The test system according to claim 9, wherein the at least one compression spring projecting from the inner side of the housing cover of the test device is supported on an outer surface of the inserted tape cassette when the housing cover is closed.

11. The test system according to claim 7, wherein the spring arrangement further comprises at least one pressure spring that can be deflected crosswise to the insertion axis to make a clamp connection on an outer surface of the tape cassette.

12. The test system according to claim 11, wherein the at least one pressure spring comprises a leaf spring and is pretensioned by a sloping face on the outer surface of the tape cassette.

13. The test system according to claim 7, wherein the inserted tape cassette is spring-loaded by the spring arrangement at least two spaced apart support points.

14. The test system according to claim 8, wherein the measuring unit engages into a free space of the tape cassette when the tape cassette is inserted into the test device in the direction of the insertion axis.

15. The test system according to claim 1, wherein the measuring unit comprises an optical measuring unit formed by a reflection-photometric measuring head mounted on the platform where the optical path of the measuring head runs crosswise to the direction of tape transport of the tape cassette located in the measuring position.

16. The test system according to claim 1, wherein the tape cassette can be connected to the tape drive of the test device by means of a coupling of the rotary drive pin, and wherein the coupling has form-fit elements that upon insertion of the tape cassette can be brought into a rotationally locked engagement position with one another by a yielding movement.

17. A tape cassette comprising a supply spool and a take-up spool and a tape guide for the defined transport of an analytical test tape between the supply spool and the take-up spool, the tape cassette being designed as a disposable for a test system according to claim 1.

18. A tape cassette comprising a supply spool and a take-up spool and a tape guide for the defined transport of an analytical test tape between the supply spool and the take-up spool, the tape cassette being designed as a disposable for a test system according to claim 7.

* * * * *